United States Patent [19]

Whiteside

[11] Patent Number: 4,467,801

[45] Date of Patent: Aug. 28, 1984

[54] METHOD AND APPARATUS FOR SHAPING A PROXIMAL TIBIAL SURFACE

[75] Inventor: Leo A. Whiteside, Chesterfield, Mo.

[73] Assignee: Wright Manufacturing Company, Arlington, Tenn.

[21] Appl. No.: 473,464

[22] Filed: Mar. 9, 1983

[51] Int. Cl.³ .............................................. A61F 5/04
[52] U.S. Cl. .............................. 128/303 R; 128/92 E; 128/305
[58] Field of Search .............. 128/92 H, 92 E, 92 EB, 128/92 EA, 92 BC, 92 CA, 92 C, 303 R, 304–305

[56] References Cited

U.S. PATENT DOCUMENTS

| | | | |
|---|---|---|---|
| 4,004,581 | 1/1977 | Heimke et al. | 128/305 |
| 4,211,228 | 7/1980 | Cloutier | 128/92 E |
| 4,271,849 | 6/1981 | Rehder | 128/305 |
| 4,273,117 | 6/1981 | Neuhäuser | 128/305 |
| 4,284,080 | 8/1981 | Rehder | 128/305 |
| 4,306,550 | 12/1981 | Forte et al. | 128/92 E |
| 4,421,112 | 12/1983 | Mains et al. | 128/92 E |

OTHER PUBLICATIONS

Dow Corning Wright "Whiteside Ortholoc TM Total Knee System," 1983.
Zimmer "Eftekhar TM II Knee Prosthesis" 1980.
Zimmer "Cloutier TM" and "Cloutier TM II," 1979, 1981.
Richards "RMC TM Total Knee System", 1978.
Total Condylar Total Knee System Tibial Cutter (Catalog No. 6737-6-300), Howmedica, Inc. Rutherford, N.J. 07070.
Howmedica ® Kinematic TM Condylar Total Knee System Tibial Guide Assembly (Catalog No. 6737-7-630), Howmedica, Inc. Rutherford, N.J. 07070.
Geo-Patella TM /Geo-Tibial TM Total Knee Alignment Instrument (Catalog No. 1348-54), Zimmer USA., Inc., Warsaw, Ind. 46580.
"The Howmedica ® Universal TM Total Knee Instrumental System", Brochure No. H-2026-1 1/82 15MB (1980); Howmedica, Inc. Rutherford, N.J. 07070.
"New Jersey Tricompartmental Total Knee Replacement Surgical Procedure by Frederick F. Buechel, M.D.," 13 pages, issue date 1/1981, Form No. 1280-32, DePuy, Div., Boehringer Mannheim Corporation, Warsaw, Ind. 46580.
Multi-Radius Total Knee Tibial Alignment Guide (Catalog No. 1360-30) from Zimmer USA., Inc. Warsaw, Ind. 46580.
T.A.R.A. TM Articular Replacement System for Hemi and Total Hip Arthroplasty, 6 pages, Form No. 779-29, issue date: 0601-44, DePuy Division of Boehringer Mannheim Corp., Warsaw, Ind. 46580.
The Modified Austin Moore Design with Porocoat TM, Surgical Procedure, 4 pages, Form No. 281-9, issue date 2/81, DePuy Division, Warsaw, Ind. 46580.

Primary Examiner—C. Fred Rosenbaum
Assistant Examiner—C. W. Shedd
Attorney, Agent, or Firm—Richard E. Rakoczy

[57] ABSTRACT

The present invention provides a method and apparatus for preparing the proximal surface of a tibia to receive a proximal tibial prosthesis employing a reamer/alignment guide which is used to internally locate the central long axis of the tibia and a plateau planar which cooperatively engages with a guide handle attached to the reamer/alignment guide to accomplish the shaping of the proximal tibial surface. The reamer/alignment guide has a rod portion extending into the interior of the tibial shaft whose central long axis corresponds with the central long axis of the tibia. The guide handle is concentric with that rod portion such that the plateau planar assumes the proper alignment with respect to the central long axis of the tibia such that the proximal tibial surface is shaped relative to that axis in a simple and accurate manner.

7 Claims, 11 Drawing Figures

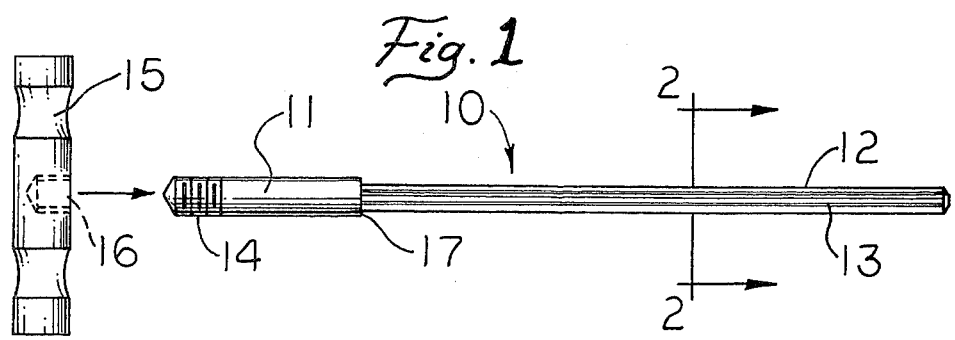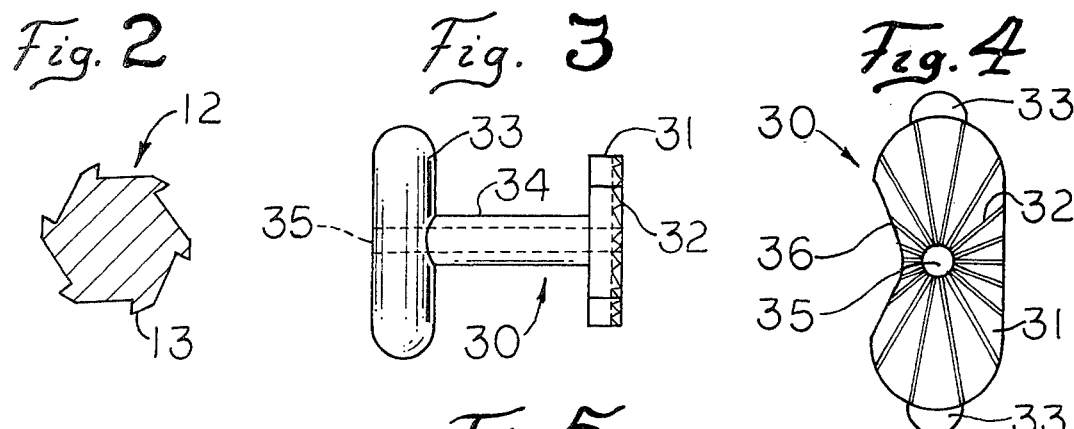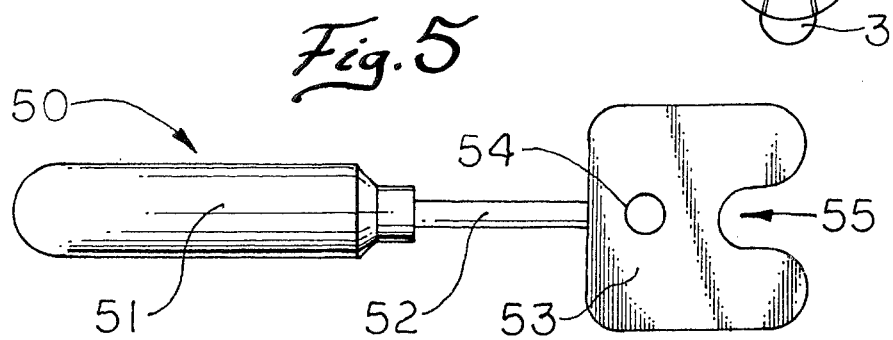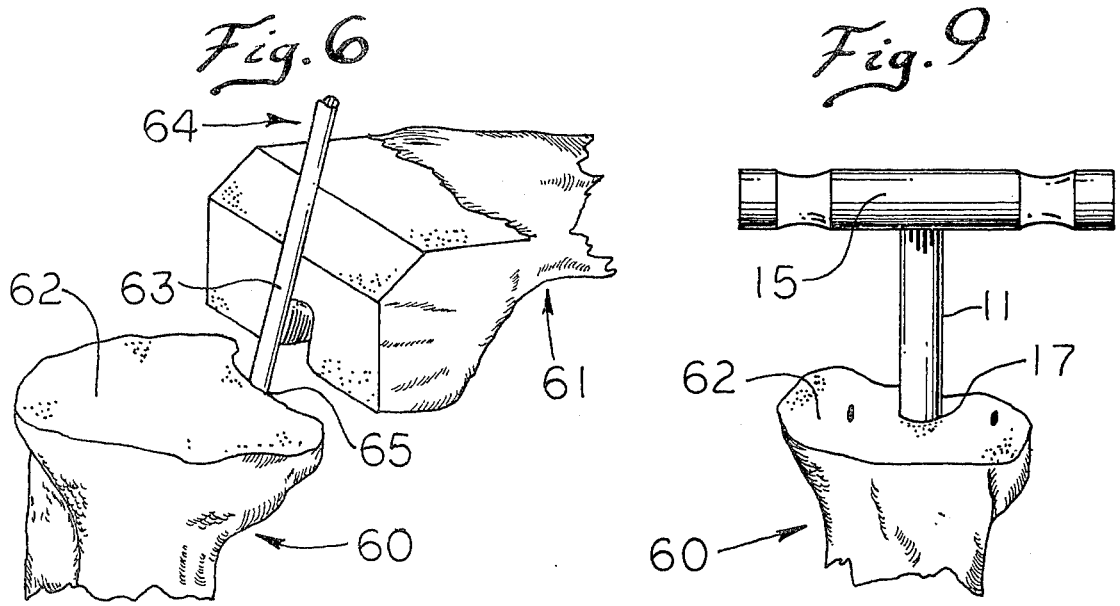

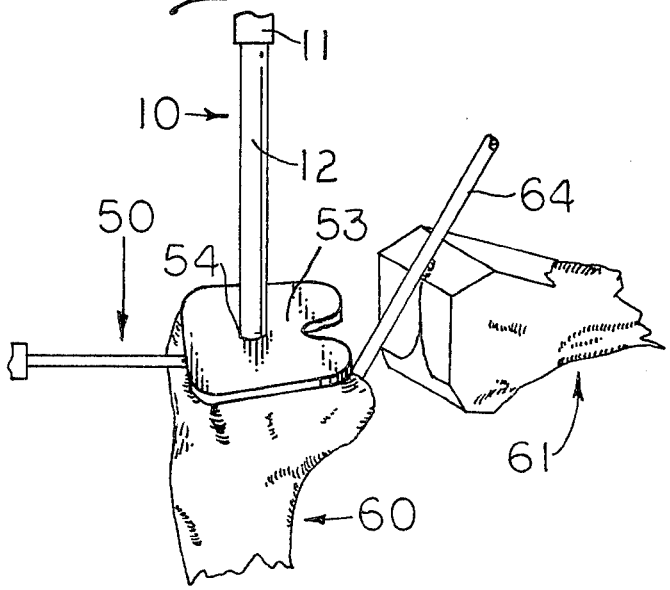
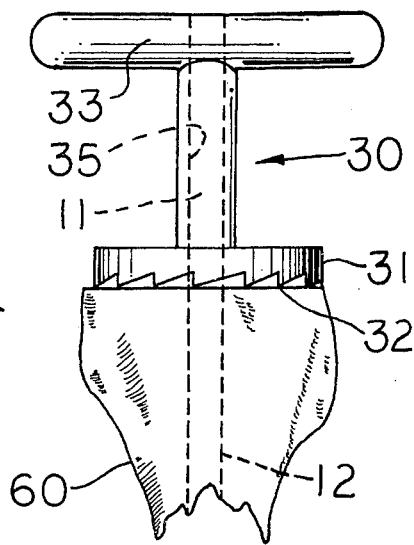
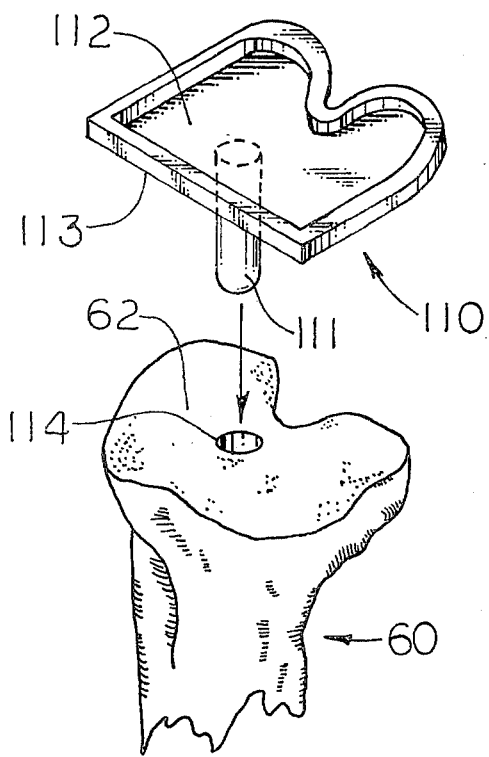
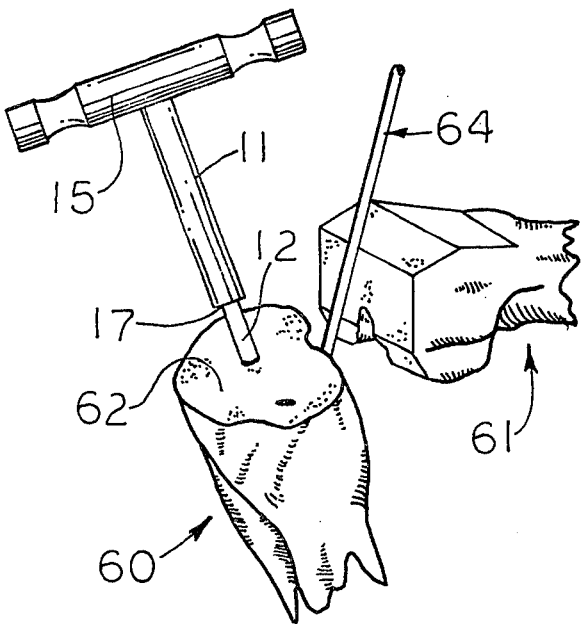

METHOD AND APPARATUS FOR SHAPING A PROXIMAL TIBIAL SURFACE

BACKGROUND OF THE INVENTION

This invention relates to a method and apparatus for shaping the proximal surface of a human tibia to receive a proximal tibial knee prosthesis employing a reamer-/alignment guide in combination with a plateau planer instrument which cooperatively engages the guide. The planer instrument modifies the proximal tibial surface transversely with respect to the central long axis of the guide and the central long axis of the shaft of the tibia.

Various types of instruments and methods have been developed to enable a surgeon to affix a proximal tibial prosthesis to the human tibia. Such methods are generally employed in conjunction with the implantation of a total knee implant involving the implantation of both a distal femoral prosthesis and a proximal tibial prosthesis which cooperate with each other to replace a diseased or otherwise defective human knee and to restore a patient's ability to walk.

It is important that each prosthesis which is implanted be attached to the femur and tibia in such a manner that it approximates as closely as possible the natural portion of the knee which the prosthesis replaces. For example, if the proximal tibial prosthesis is not properly affixed with respect to the central long axis of the tibial shaft, an unnatural gait or other complications can result.

It is a common practice to use the long central axis of the femur as an alignment guide to determine the proper manner in which a distal femoral prosthesis is to be attached to the femur. The central long axis of the shaft of the tibia is then located and the proximal surface of the tibia is horizontally resected and prepared to receive a proximal tibial prosthesis which typically is chosen to lie in the plane of the transverse axis of the knee. If the tibial surface does not lie in the plane chosen, the implanted prosthesis may not properly align with the distal femoral prosthesis and complications can result.

One example of a method and apparatus for resecting the proximal tibial surface which employs external alignment guides situated outside of the flesh covering the femur and the tibia can be found in the "The HOWMEDICA ® Universal ™ Total Knee Instrument System", brochure no. H-2026-1 1/82 15M B (1980) from Howmedica, Inc., Orthopaedics Division, Rutherford, NJ 07070 which is hereby incorporated by reference. Another method which employs a tibial resection guide which is fixed to both the distal femoral surface and to the tibia by means of pins and employs an external alignment rod situated outside of the skin over the tibia is shown in a brochure entitled "New Jersey Tricompartmental Total Knee Replacement Surgical Procedure by Frederick F. Buechel, M.D.", 13 pages, issue date 1/1981, Form No. 1280-32, from DePuy Division, Boehringer Mannheim Corporation, Warsaw, Ind. 46580. Other examples of instruments which are intended to rest against the outside of the long axis of the tibia are the MULTI-RADIUS total knee tibial alignment guide (Catalog No. 1360-30) from Zimmer USA, Inc., Warsaw, Ind. 46580 and the Total Condylar Total Knee System tibial cutter (Catalog No. 6737-6-300) and HOWMEDICA ® KINEMATIC ™ Condylar Total Knee System tibial guide assembly (Catalog No. 6737-7-630), both of which are products of Howmedica, Inc., Orthopaedics, Division. Still another tibial alignment instrument in Catalog No. 1348-54 from Zimmer USA, Inc. which is inserted into the fixation holes for the femoral component of the GEO-PATELLA ™/GEO-TIBIAL ™ total knee and employs an external guide which is aligned with the tibia to mark the points where the resection should be made.

External alignment instruments have a disadvantage in that the surgeon is relying upon visual and tactile means for positioning the alignment means since the patients's skin covers the major portion of the tibia and screens it from view. Locating the shaft of the tibia of an obese person or of a person having a deformity of the tibia which may somewhat alter its true central axis can present further difficulties.

SUMMARY OF THE INVENTION

There appears to be a need for a method of shaping the proximal surface of a tibia to receive a proximal tibial prosthesis which enables a surgeon to shape that surface as accurately as possible while using the central long axis of the shaft as a guide.

One object of the present invention is to provide a means by which the central long axis of the shaft of the tibia can be more accurately determined through the use of an instrument passing through the center of the shaft of the tibia.

It is another object of the present invention to provide a reamer/alignment guide upon which a plateau planer for the proximal surface of the tibia can be mounted such that the alignment of the abrading surface of the planer is always made relative to the central long axis of the shaft of the tibia.

It is yet another object of the present invention to provide a plateau to accomplish the shaping of the proximal tibial surface to obtain a much smoother and accurately planed surface than is typically obtained with an oscillating saw. That accurately planed, level surface is highly desirable when a proximal tibial prosthesis employing a cementless fixation means such as a porous ingrowth coating is to be affixed to the tibia.

It is still another object of the present invention to provide a method for overcoming the detrimental effects which deformities cause in locating the central long axis of the tibia and thereby enable a surgeon to more accurately shape the proximal surface of such a tibia to receive a proximal tibial prosthesis.

These and other objects of the present invention are provided by a method which comprises preparing the proximal tibial surface; determining the approximate location where the central long axis of the tibia (lying along the center of the interior of the tibial shaft) passes through the proximal tibial surface; advancing a reamer/alignment guide through that location for a sufficient distance along the interior of the tibial shaft to allow the central long axis of the tibia to correspond to that of the reamer/alignment guide; attaching a plateau planer to the handle of the reamer/alignment guide; modifying the proximal tibial surface using the plateau planer; trimming any remaining bone from the proximal tibial surface to obtain a smooth flat surface on which a tibial prosthesis can be affixed; and removing the reamer/alignment guide.

This invention also provides a reamer/alignment guide in combination with a plateau planer which cooperatively engages with the reamer/alignment guide and enables the proximal tibial surface to be shaped in a planer fashion transverse to the central long axis of the tibia. The invention also provides a plateau planer having a planer abrading surface, a handle and a shaft connecting the two.

BRIEF DESCRIPTION OF THE DRAWINGS

The above and other objects, features and advantages of the present invention will become apparent to those skilled in the art upon an examination of the following description and drawings which are merely illustrative of the present invention.

In the Drawings

FIG. 1 is an exploded plan view of a preferred reamer/alignment guide and its handle.

FIG. 2 is a cross-section taken along section line 2—2 of FIG. 1.

FIG. 3 is a side view of a preferred plateau planer.

FIG. 4 is a view of FIG. 3 taken from below.

FIG. 5 is a plan view of a tibial reamer insertion guide.

FIG. 6 is a perspective view of the tibia and femur being separated.

FIG. 7 is a perspective view showing the marking of the approximate location for the entry of the reamer/alignment guide.

FIG. 8 is a perspective view from the side showing the advancement of reamer/alignment guide into the tibial shaft.

FIG. 9 is a perspective view of the reamer/alignment guide fully advanced into the tibial shaft.

FIG. 10 is a frontal perspective view showing the plateau planer in place.

FIG. 11 is an exploded perspective view taken from the side showing placement of a proximal tibial prosthesis in the hole left by the reamer/alignment guide.

DETAILED DESCRIPTION OF THE INVENTION

Referring to the Drawings, FIG. 1 depicts a preferred form of a reamer/alignment guide 10 which is a rod having a first portion 12 which is intended to enter the interior of the tubluar shaft of the tibia which is an interior region bounded by hard compact (cortical) bone. Portion 12 has a plurality of cutting ridges 13 situated about its circumference. Portion 12 has an outer diameter (including the cutting ridges) of such a dimension that it approximates the narrowest portion of the interior of the tibial shaft. FIG. 2 shows the portion 12 and the cutting ridges 13 in cross-section.

In the preferred embodiment shown, six cutting ridges are equidistantly situated about the circumference of portion 12. The remaining portion of reamer/alignment guide 10 is preferably a smooth portion 11 of a slightly larger diameter than portion 12 which is intended to contact the proximal tibial surface and thereby indicate when the reamer is fully inserted within the interior of the tibial shaft as will be described infra. The end of portion 11 contains threads 14 or some other means by which opening 16 of handle 15 may be fitted over and secured to the end of portion 11 as a means to enable a twisting motion to be imparted to reamer/alignment guide 10 during use. In a preferred embodiment, portion 12 is 10" (254 mm) in length and 0.359" (9.12 mm) in outer diameter from the top at one cutting ridge to the ridge opposite it) and portion 11 is about 3.6" (91 mm) in length and 0.495" (12.6 mm) in outer diameter where the symbol " means inches and the symbol mm means millimeters. For use with a tibia having a significant degree of deformity, a reamer wherein portion 12 is 7" (178 mm) can be used.

Portion 11 also serves a second purpose as a guide handle for the hereinafter described plateau planer. Portion 11 (hereinafter —guide handle 11")is concentric with first portion 12 of guide 10 and when guide 10 is advanced a sufficient distance through the interior of the tibial shaft until portion 12 is aligned with the long central axis of the tibia, the long central axis of guide handle 11 also lies along the long central axis of the tibia. If it is desired, other instruments for the guiding of shaping instruments or for use in directly shaping the proximal tibial surface can also be attached to guide handle 11 such that shaping operations using such instruments can be carried out relative to the central long axis of the tibia.

FIG. 3 shows a plateau planer having a planar abrading surface 31 which, in the preferred embodiment shown, possesses a plurality of spaced cutting ridges 32 which are planar and are situated transverse to the central long axis of guide handle 11 (not shown). Guide handle 11 is inserted through passage 35 which is adapted to cooperatively engage handle 11 thereby enabling the plateau planer 30 to be freely rotated against the proximal tibial surface (not shown) about the central long axis of the guide handle 11 and thus rotated about the central long axis of the shaft of the tibia. Planar abrading surface 121 is rotated about the proximal tibial surface by imparting a twisting motion to handle 33 which is attached to abrading surface 121 by means of shaft 124. Passage 35 preferably has a 0.500" (12.7 mm) diameter when preferred guide handle 11 having a 0.495" (12.6 mm) outer diameter is employed.

FIG. 4 shows plateau planer 30 from below and more clearly shows the preferred configuration of cutting ridges 32 found on abrading surface 31 and their relationship to passage 35 and handle 33. Also shown is recessed area 36 in plateau planer 120 which is included to avoid trauma to anatomical members found about the intercondylar fossa of the proximal tibial surface.

The preferred configuration of the plateau planer is the one shown in FIGS. 3 and 4 wherein (a) handle 33 is situated above and parallel to planar abrading surface 31, (b) shaft 34 is transverse to both planar abrading surface 31 and to handle 33 and (c) passage 35 extends through the centers a planar abrading surface 31, shaft 24 and handle 33.

The above described reamer/alignment guide, plateau planer and components thereof are all preferably manufactured from a suitable surgical grade of stainless steel of the type commonly employed by those skilled in the art to construct surgical tools for use in contact with the body. The exact composition of the metal from which the guide, planer and components thereof are constructed forms no part of the present invention and other metals suitable for use within the body and for the intended uses of the guide, planer and the like may be used without altering the nature of the invention.

It should also be noted that another advantage of the present invention is that the above-described reamer/alignment guide and plateau planer can be used in modifying the surface of either the right or the left proximal tibial surface.

Fig. 5 shows a proximal tibial surface reamer insertion guide 50 having handle 51 and guideplate 53 interconnected by means of arm 52. Guideplate 53 is of such a configuration that it is designed to approximate the outline of the superior proximal surface of the tibia and to rest thereon such that when guideplate 53 is placed on that superior surface, the surface of guideplate 53 opposite handle 51 is lined up with the posterior aspects of the medial and lateral tibial condyles and recess 55 corresponds to the posterior intercondyloid fossa of the tibia. Hole 54 is of the same diameter as is portion 12 of guide 10 and is placed on guideplate 53 during its manufacture in a location which is such the the approximate central long axis of the tibia passes through hole 53. Since tibias differ in size, several guideplates of varying sizes may be provided and the one which most closely corresponds to the outline of the proximal tibial surface to be shaped is used. The exact center of hole 54 need not correspond exactly to that of the central long axis of the tibia since the reamer/alignment guide will adjust the entry point to correspond to that axis as will be described infra. Guide 50 can be manufactured from the same type of metals previously described for the reamer/alignment guide.

The manner in which the method of the present invention may be carried out will now be described. The proximal tibial surface is most often reshaped pursuant to the implantation of a total knee implant involving prostheses which are attached to the distal femoral surface and the proximal tibial surface. The present method and apparatus for shaping the proximal tibial surface described herein is advantageously and preferably employed in conjunction with the method and apparatus described in my copending U.S. patent application Ser. No. 473,465 entitled "Method and Apparatus For Shaping a Distal Femoral Surface" which is being filed concurrently herewith in the name of Leo Allen Whiteside (which application is hereby incorporated by reference). The method described in that patent application can be combined with that of the present invention to produce appropriately shaped distal femoral and proximal tibial surfaces to which the appropriate prostheses can be attached during total knee implantation surgery.

Preferably, the appropriate preoperative procedures of the type described in my copending patent application are followed.

Operatively, the usual surgical approach is made. After the anterior aspect of the knee is exposed, the knee is flexed to 100° so that the posterior curved surfaces of both femoral condyles can be visualized. Partial excision of the fatpad may be necessary. The preceding operative approach is not illustrated and for the purposes of clarity, soft tissue, ligaments and other nonessential elements have been eliminated from FIGS. 6–11.

Preferably, the distal femoral surface is shaped first in accordance with the procedure described in my aforementioned patent application if a total knee prosthesis is to be implanted. The details of that method are found in that patent application which is incorporated by reference and will not be repeated here. FIG. 6 shows distal femur 61 which was shaped in accordance with that method.

The shaping of the proximal tibial surface is begun by using an oscillating saw to resect a small amount of the superior proximal surface of the tibia to form an approximately planar surface 62 as is generally shown in FIG. 6. The surface 62 need not be absolutely planar because the purpose is to provide a relatively flat surface upon which the plateau planer will be placed to produce a planar surface as described infra. Care should be taken to remove as little bone as is appropriate. In varus knees with a depressed proximal medial tibial plateau, the hard cortical bone is left intact and the surface of the proximal lateral tibial plateau is removed with an oscillating saw. In valgus knees with a depressed proximal lateral tibial plateau, the lateral cortical weight bearing surface is left intact and the proximal medial tibial surface is removed with the oscillating saw. The anterior cruciate ligament and the posterior segments of the menisci (not shown) are removed from the upper tibial surface.

Referring again to FIG. 6, a lever type retractor 64 is inserted just lateral to the tibial attachment of the posterior cruciate ligament and the retractor 64 is placed in the intercondylar notch 63 of the right femur 61. The roughly flattened superior proximal surface 62 of right tibia 60 is levered forward to expose the entire superior proximal tibial surface 62.

Guideplate 53 of tibial reaming guide 50 is placed on surface 62 as shown in FIG. 7. The bottom of guideplate 53 may have small pins or some other means extending away from its lower surface (not shown) which engage surface 62 and hold guideplate 53 in place. The distal tip of portion 12 of reamer/alignment guide 10 is inserted into hole 54 and portion 12 is used to mark the location at which reamer/alignment guide 10 is to be advanced into the tibia 60 by turning guide 10 from side to side or by striking it with a mallet.

After marking the location for the entry of portion 12, guide 50 is removed and portion 12 of reamer/alignment guide 10 is advanced through surface 62 into the interior of the shaft of the tibia as shown in FIG. 8. Insertion of reamer/alignment guide 10 often requires alternate turning of guide 10 and striking of the handle 15 with a mallet. Guide handle 11 is of a slightly larger outer diameter than that of portion 12 and the boundary between the two is shown as surface 17.

FIG. 8 shows guide 10 advancing through surface 62 with the central long axis of portion 12 and handle 11 in a somewhat exaggerated fashion relative to the central long axis of the tibia 60. This illustrates one advantage of using the reamer/alignment guide of the present invention. At times, portion 12 will advance through the cancellous bone of the proximal tibial surface 62 as it is inserted. This occurs because the proximal surface of a tibia is not always aligned directly over the isthmus of a tibia and the location marked by hole 54 on guideplate 53 does not correspond to the central long axis of the tibia. As long as the reamer/alignment guide engages the isthmus of a tibia, it will advance through the interior of the tibial shaft through the softer interior that is bounded by the harder compact bone of the tibial shaft if a reasonable, but not excessive, amount of force is used to turn the handle 15 of guide 10 and advance it. As portion 12 follows the interior of the tibial shaft, it is brought into alignment with the central long axis of the tibia. Portion 12 also exerts a lateral reaming action on the proximal tibial surface 62 such that the entry point is moved laterally until the central axis of guide 10 extends through surface 62 at a location which corresponds to the central long axis of tibia 60. The passage left in surface 62 upon later removal of guide 10 can then be used as a point for the insertion of the retention stem of a proximal tibial prosthesis.

FIG. 9 shows guide 10 fully advanced into tibia 60 with surface 17 of handle 11 contacting proximal tibial surface 62.

Handle 15 is removed from guide handle 11 and plateau planer 30 is inserted over guide handle 11 with planar abrading surface 31 having planar cutting ridges 32 placed against surface 62 of tibia 60 as shown in FIG.

10. Plateau planer 30 cooperatively engages handle 11 and aligns with the central long axis of reamer/alignment guide 10 which is shown in outline form as first portion 12 and guide handle 11, the latter of which passes through passage 35 of planer 30. Proximal tibial surface 62 is shaped to a smooth, planar surface which is transverse to the central long axis of the tibia by grasping handle 33 and twisting it from side to side as planar abrading surface 31 is held against surface 62 of tibia 60.

This operation typically leaves hard cortical bone on either the medial or the lateral proximal tibial surfaces which may be removed with an oscillating saw. Occasionally it is necessary to use an oscillating saw to trim down the sclerotic proximal tibial surface in order to facilitate planing.

After a smooth, planar, proximal tibial surface is obtained, the reamer/alignment guide is removed. In some cases it may be necessary to remove a small ridge of bone from the periphery of the planed proximal tibial surface 62. The implantation of one of a number of well known proximal tibial prostheses can then proceed along with the attachment of an appropriate distal femoral prosthesis.

The plateau planer produces a much smoother and planar surface than is usually the case with an oscillating saw because such saws tend to ride over hard bone and cut into the softer areas on the tibial surface. The plateau planer cannot ride over the hard bone and results in a very level and accurately planed surface because the guide handle 11 holds planar abrading surface 31 in place. The resulting planar surface provides a firm mounting for a prosthesis and enables the maximum amount of proximal tibial surface to contact the surface of a proximal tibial prosthesis.

The passage 114 in tibia 60 which is left when portion 12 is removed corresponds to the central long axis of tibia 60 and, as shown in FIG. 11, provides a convenient location in which the stem 111 of a proximal tibial prosthesis 110 having upper surface 112 whch articulates the distal femoral prosthesis and a lower surface 113 which rests against surface 62 of tibia 60. Depending upon the type of total knee implant chosen, it may be preferable to affix the distal femoral prosthesis prior to affixing the proximal tibial prosthesis, but the order of affixation should not affect the method of the present invention. After implantation of the prosthesis or prostheses in accordance with the usual surgical procedures, the wound is closed in the usual fashion.

Other modifications and variations of the method and apparatus of the present invention will become apparent to those skilled in the art from an examination of the above specification and drawings. Therefore, other variations of the present invention may be made which fall within the scope of the appended claims even though such variations were not specifically discussed above.

That which is claimed is:

1. A method of preparing a human tibia having a superior proximal surface and a central long axis defined by the interior of a tubular shaft of hard compact bone to receive a superior proximal tibial knee prosthesis, said method comprising the steps of
    (A) resecting a small amount of the superior proximal surface of the tibia to form an approximately planar surface which is approximately transverse to the central long axis of the tibia,
    (B) determining the approximate location on the superior proximal surface of the tibia which corresponds to the central long axis of the tibia,
    (C) advancing a reamer/alignment guide through said superior proximal surface at said location along the interior of said tubular shaft of the tibia for a sufficient distance to enable the central long axis of said reamer/alignment guide to correspond with the central long axis of the tibia, said reamer-/alignment guide comprising a rod having a first portion which is intended to enter the interior of said tubular shaft of the tibia which portion (1) is of an outside diameter approximating the narrowest portion of said interior and (2) has a plurality of cutting ridges situated about its circumference, the remaining portion of said rod acting as a guide handle which extends outwardly from said proximal surface and is concentric with the central long axis of said first portion, said handle further having a means thereon for imparting a twisting motion to said reamer/alignment guide,
    (D) attaching a plateau planer to said guide handle, said planer comprising a planar abrading surface, a handle and a shaft connecting said planar abrading surface to said handle, said planer having a passage therethrough adapted to cooperatively engage said guide handle and to allow the planar abrading surface to be transversely rotated about the central long axis of said guide handle while it is in contact with the proximal surface of said tibia to flatten said proximal surface transversely with respect to the central long axis of the guide handle, said planar abrading surface containing a plurality of space cutting ridges which are planar and are situated transverse to the central long axis of said guide handle and further having a recessed area thereon to avoid trauma to anatomical members found about the intercondylar fossa of the proximal surface of the tibia,
    (E) modifying said proximal surface of the tibia through the use of said planer until said surface is smooth, planar and transverse to the central long axis of said guide handle,
    (F) trimming any remaining bone from the proximal surface of the tibia to present a smooth, flat surface on which a proximal tibial prosthesis can be affixed, and
    (G) removing the reamer/alignment guide.

2. The method as claimed in claim 1 wherein in step (C), said guide handle has a smooth outer surface and has an outer diameter which is larger than that of said first portion.

3. The method as claimed in claim 1 wherein in step (D), the handle of said planer is situated above and parallel to said planar abrading surface, said shaft is transverse to both the planar abrading surface and to the handle, and said passage extends through the center of said planer abrading surface, said shaft and said handle.

4. As an article of manufacture, a proximal tibial surface cutting guide comprising the combination of
    (A) a reamer/alignment guide comprising a rod having a first portion adapted to enter the interior of the tubular shaft of a tibia in such a manner that the central long axis of said first rod portion corresponds to the central long axis of the tibia, said first rod portion (1) being of an outside diameter approximating the narrowest portion of said interior and (2) having a plurality of cutting ridges situated about its cicumference, the remaining portion of said rod being a guide handle which is concentric with the central long axis of said first portion and further has a means thereon for imparting a twisting motion to said reamer alignment guide, with (B) a plateau planer comprising a planar abrading surface, a handle and a shaft connecting said planar abrading surface to said handle, said planer having a passage therethrough adapted to cooperatively engage said guide handle and to allow the planar abrading surface to be transversely rotated about the central long axis of said guide handle while it is in contact with the proximal surface of said tibia to flatten said proximal surface transversely with respect to the central long axis of the guide handle, said planar abrading surface containing a plurality of spaced cutting ridges which are planar and are situated transverse to the central long axis of said guide handle and further having a recessed area thereon to avoid trauma to anatomical members found about the intercondylar fossa of the proximal surface of the tibia.

5. The article as claimed in claim 4 wherein in (B), the handle of said planer is situated above and parallel to said planar abrading surface, said shaft is transverse to both the planar abrading surface and to the handle and said passage extends through the center of said planar abrading surface, said shaft and said handle.

6. As an article of manufacture, a plateau planer for modifying the proximal surface of a human tibia comprising a planar abrading surface, a handle and a shaft connecting said planar abrading surface to said handle, said planer havig a passage therethrough adapted to cooperatively engage a guide handle of a tibial alignment guide and to allow the planar abrading surface to be transversely rotated about the central long axis of said guide handle while it is in contact with the proximal surface of said tibia to flatten said proximal surface transversely with respect to the central long axis of the guide handle, said alignment guide being adapted to pass through the central long axis of a tibia wherein said guide handle is situated on said alignment guide in such a manner that said central long axis of the tibia corresponds with the central long axis of the guide handle, said planar abrading surface containing a plurality of spaced cutting ridges which are planar and are situated transverse to the central long axis of said guide handle and further having a recessed area thereon to avoid trauma to anatomical members found about the intercondylar fossa of the proximal surface of the tibia.

7. The article as claimed in claim 6 wherein the handle of said planer is situated above and parallel to said planar abrading surface, said shaft is transverse to both the planar abrading surface and to the handle and said passage extends through the center of said planar abrading surface, said shaft and said handle.

* * * * *

UNITED STATES PATENT AND TRADEMARK OFFICE
CERTIFICATE OF CORRECTION

PATENT NO. : 4,467,801
DATED : August 28, 1984
INVENTOR(S) : Leo A. Whiteside

It is certified that error appears in the above-identified patent and that said Letters Patent is hereby corrected as shown below:

In column 2, line 34, "plateau to" should read
-- plateau planer to --.

In column 3, line 42, "tubluar" should read -- tubular --.

In column 3, line 65, "it)" should read -- it --.

In column 4, line 46, "a planar" should read -- of planar --.

In column 4, line 47, "24" should read -- 34 --.

In column 5, line 8, "the the approximate" should read
--that the approximate --.

In column 10, line 5, "havig" should read -- having --.

Signed and Sealed this

Fourteenth Day of October, 1986

[SEAL]

*Attest:*

DONALD J. QUIGG

*Attesting Officer*  *Commissioner of Patents and Trademarks*